United States Patent [19]

Takanohashi et al.

[11] Patent Number: 4,794,182
[45] Date of Patent: Dec. 27, 1988

[54] 2-ALKYL-4-AMINO-5-AMINOMETHYL-PYRIMIDINES

[75] Inventors: Kunio Takanohashi, Kawanishi; Toru Yamano, Itami; Mitsutaka Tanaka, Sanda, all of Japan

[73] Assignee: Takeda Chemical Industries, Ltd., Osaka, Japan

[21] Appl. No.: 73,697

[22] Filed: Jul. 14, 1987

[30] Foreign Application Priority Data

Jul. 14, 1986 [JP] Japan .................. 61-166501

[51] Int. Cl.$^4$ .......................... C07D 239/42
[52] U.S. Cl. ........................ 544/326; 544/329
[58] Field of Search ............. 544/330, 332, 326, 329

[56] References Cited

U.S. PATENT DOCUMENTS 4,536,577 8/1985 Yoshida et al. ............... 544/326
4,539,403 9/1985 Fujii et al. .................... 544/326

FOREIGN PATENT DOCUMENTS 190975 10/1984 Japan .

OTHER PUBLICATIONS

Kozo et al., Chemical Abstracts, vol. 99, entry 175794h (1983).
Ube Industries., Chemical Abstracts, vol. 101, entry 90962w (1984).
Ube Industries., Chemical Abstracts, vol. 102, entry 149287f (1985).

Primary Examiner—John M. Ford
Attorney, Agent, or Firm—Wenderoth, Lind & Ponack

[57] ABSTRACT

A novel 2-lower alkyl-4-amino-5-substituted iminopyrimidine compound represented by the formula:

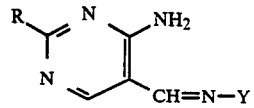

wherein R is a lower alkyl, and Y is hydroxyl or amino which may be protected or a salt thereof is obtainable by allowing a formylpyrimidine compound represented by the formula:

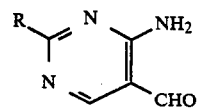

wherein R is a lower alkyl to react with a compound represented by the formula H$_2$N—Y, wherein Y is hydroxyl or amino which may be protected, or a salts thereof. The iminopyrimidine compound gives the known pyrimidine compound represented by the formula:

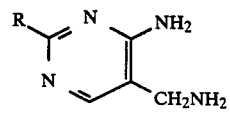

wherein R is as defined above in high yield. Therefor, the process is very useful as an industrial production method.

6 Claims, No Drawings

2-ALKYL-4-AMINO-5-AMINOMETHYLPYRIMIDINES

This invention relates to a novel 2-lower alkyl-4-amino-5-substituted iminopyrimidine compound and to a process of preparing, with an industrial advantage, 2-lower alkyl-4-amino-5-aminomethylpyrimidine which is one of the important intermediates of synthesizing vitamin $B_1$.

2-Lower alkyl-4-amino-5-aminomethylpyrimidine is one of the important intermediates of synthesizing vitamin $B_1$ or its analogous compounds. As methods of preparing this pyrimidine compound, there have widely been known, for example, a method of subjecting 2-lower alkyl-4-amino-5-cyanopyrimidine to reduction or a method of subjecting 2-lower alkyl-4-amino-5-acetamidomethylpyrimidine to hydrolysis, etc. Recently, there is a report referring to a method which comprises allowing 2-lower alkyl-4-amino-5-formylpyrimidine to react with ammonia, followed by subjecting the resultant to catalytic reduction in the presence of a catalytic reduction catalyst (U.S. Pat. No. 4,539,403; patented on Sept. 3, 1985). This method employing 5-formylpyrimidine as the starting material is considered to be very advantageous as an industrial method, because an industrially advantageous catalytic reduction is utilized and this starting material can be prepared from acrylonitrile.

However, the above-mentioned catalytic reduction method using ammonia produces, besides the object compound, not a little amount of by-products such as 2-methyl-4-amino-5-hydroxymethylpyrimidine, di(2-methyl-4-amino-5-pyrimidylmethyl)amine, 2-methyl-4-amino-5-pyrimidylmethylidene-(2-methyl-4-amino-5-pyrimidylmethyl)amine (Schiff base), etc. This invites lowering of the yield, complicated processes of refining, etc., thus much room has been left for improvement. Circumstances being such as above, for solving the problems, there have been proposed a method which comprises allowing for example phosphorus molybdate to coexist in the process of allowing 5-formyl pyrimidine to react with ammonia (U.S. Pat. No. 4,536,577; patented on Aug. 20, 1985), or a method which comprises allowing a hydroxide of an alkali metal or alkaline earth metal to coexist together with ammonia in the process of catalytic reduction (Publication No. of Unexamined Japanese Patent Application 190,975/1984). By these improved methods, formation of the by-products is suppressed to some extent, but these by-products are still formed in an amount of about 5%, thus the defect has not been dissolved satisfactorily.

The present inventors, after studies on the method of preparing 2-lower alkyl-4-amino-5-aminomethylpyrimidine from 2-lower alkyl-4-amino-formylpyrimidine, found that the formation of by-products can be suppressed to less than 1%, by allowing hydroxylamine or a hydrazine derivative to react with the starting material to give 2-lower alkyl-4-amino-5-pyrimidine aldoxime or hydrazone, followed by subjecting this aldoxime or hydrazone to catalytic reduction. Catalytic reduction of oxime or hydrazone is generally well known reaction, and this reaction usually gives a plurality of reduced products. On the other hand, in the present invention, formation of by-products can be substantially suppressed to obtain only the object compound selectively, which is in fact a surprising finding. Based on this finding, the present inventors carried out further studies to complete the present invention.

The present invention relates to (1) a compound representable by the general formula:

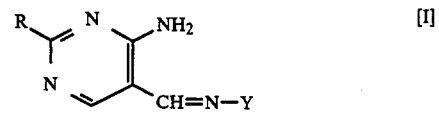

wherein R stands for a lower alkyl, and Y stands for a hydroxyl group or an amino group which may be protected, or salts thereof;

(2) a process of preparing a pyrimidine compound representable by the general formula:

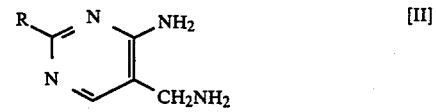

wherein R is as defined above, or a salt thereof, which comprises subjecting a compound representable by the formula [I] to catalytic reduction; and (3) a process of preparing a pyrimidine compound representable by the formula [II], which comprises allowing a formylpyrimidine compound representable by the general formula:

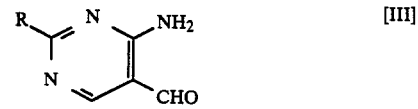

wherein R stands for a lower alkyl to react with a compound [IV] representable by the general formula $H_2N-Y$, wherein Y stands for a hydroxyl group or an amino group which may be protected, or a salt thereof to give a compound representable by the formula [I], then by subjecting the resulting compound to catalytic reduction.

In the compounds [I], [II] and [III], the lower alkyl group representable by R includes, for example, $C_{1-4}$ alkyl such as methyl, ethyl, propyl, butyl, etc., the protecting group of the optionally protected amino group representable by Y includes, for example, a lower alkyl($C_{1-4}$)carbonyl such as acetyl, propionyl, butyryl, etc., a lower alkyl($C_{1-3}$) such as methyl, ethyl, propyl, etc., and aryl such as phenyl. The representative of the optionally protected amino group is a phenyl-substituted amino group. Salts of the compound [I] includes, for example, those of inorganic acids, such as hydrochloride, sulfate, phosphate, etc. The compound [I] comprises syn- and anti-isomers and mixtures thereof, and these are all within the scope of the compound [I]. The compound [I] of the present invention includes an oxime in which Y is a hydroxyl group and a hydrazone in which Y is an amino group which may be protected. Typical compounds among them are oxime compounds in which R is methyl and Y is a hydroxyl group, or salts thereof. The compound [I], especially oximes thereof are specifically useful as intermediates for synthesizing 2-lower alkyl-4-amino-5-aminomethylpyrimidine.

The compounds of the formula [I] are novel compounds which have never been reported on literature references, and they can be prepared by allowing a formylpyrimidine representable by the general formula [III] to react with a compound representable by the general formula [IV].

The formylpyrimidine compound [III] is a known substance described in Publication No. of Unexamined Japanese patent application: 134,082/1983, which can be prepared by, for example, subjecting 2-lower alkoxy methylene-3,3-dialkoxy propane nitrile and an amidine compound (e.g. acetamidine, etc.) to ring closure reaction, followed by subjecting the resultant 2-lower alkyl-4-amino-5-dialkoxymethylpyrimidine to hydrolysis. This material compound [III] is usually employed in the free state, but it can be used in the form of a salt of an inorganic acid such as sulfuric acid, nitric acid, hydrochloric acid, phopsphoric acid, etc. As one of such materials as above, 2-methyl-4-amino-5-formylpyrimidine or salts thereof can be exemplified. As an example of the compound [IV] can be mentioned hydroxylamine in which Y is a hydroxyl group. This hydroxylamine may be used in the form of a salt of an inorganic acid, such as hydrochloride, sulfate, etc. Furthermore, the compound [IV] is exemplified by hydrazine in which Y is amino, and hydrazines in which this amino group is protected with, for example, a lower alkyl($C_{1-4}$)carbonyl (e.g. acetyl hydrazine or propionyl hydrazine), with aryl such as phenyl (e.g. phenyl hydrazine) or with a lower alkyl($C_{1-3}$) such as methyl, ethyl, propyl (e.g. methyl hydrazine, ethyl hydrazine). These compounds, like the hydroxylamine, may be used in the form of a salt of an inorganic acid. The amount of the compound [IV] is sufficient in 1 mole or more, usually about 1 to 1.3 mol. relative to 1 mole of the compound [III].

The reaction between the compound [III] and the compound [IV] is carried out in water or an inert organic solvent containing water. As the organic solvent, use is made of, for example, alcohols such as methanol, ethanol, propanol, ethylene glycol, etc.; ethers such as dioxane, tetrahydrofuran, etc.; nitriles such as acetonitrile, propionitrile, etc.; amides such as N,N-dimethylformamide, N,N-dimethylacetamide, etc. The volume of any of the above-exemplified organic solvents to be mixed with water is not limitative, but usually 5% or more is preferable. The volume of the solvent is not limitative, but it is usually in the range of about 3 to 50 weight parts relative to 1 weight part of the starting 5-formylpyrimidine. The reaction temperature is in the range of from 0° C. to 100° C., preferably from room temperature to 60° C. The reaction completes usually in 0.5 to 5 hours. This reaction proceeds in acid to neutral conditions. When a salt is employed as the starting material, the reaction may be allowed to proceed after neutralizing with the addition of an alkali such as sodium carbonate. In this case, the object product is given as the free form. Addition of a small amount of an acid, for example, an inorganic acid such as hydrochloric acid, sulfuric acid, nitric acid, phosphoric acid, etc., or an organic acid such as acetic acid, oxalic acid, etc. to the reaction system serves to further accelerate the reaction rate. The amount of the acid to be added is sufficient in 0.5 mole or less relative to 1 mole off the starting 5-formylpyrimidine.

For separation and purification of the compound [I] from the reaction mixture, conventional means, for example, concentration, neutralization, extraction, recrystallization, etc. can be suitably employed. The compound [I] is usually produced as a mixture of anti- and syn-compounds. The anti-compound and the syn-compound can be, when necessary, separated from each other by such means as, for example, recrystallization, chromatography, etc.

According to the above-mentioned method, even when the starting 5-formylpyrimidine contains impurities, the object compound can be produced in a pure state and substantially quantitatively, because the reaction between the formyl group and the compound [IV], especially hydroxylamine, proceeds specifically and quantitatively. Therefore, in this method, 5-formylpyridmine containing impurities can be employed as it is as the starting material. For example, 2-methyl-4-amino-5-formylpyrimidine can be prepared by subjecting 2-alkoxymethylene-3,3-dialkoxypropane nitrile and acetamidine to ring closure reaction in alcohol (e.g. methanol), followed by hydrolysis. This hydrolyzate solution can be used as it is as the material of the above-mentioned method.

The novel compound [I] is subjected to catalytic reaction with hydrogen in a reducing catalyst in an inert solvent to thereby prepare a compound representable by the formula [II].

The starting material [I] to be employed in this reaction can be either in the free state or in the form of a salt, and, it may be a mixture of anti- and syn-compounds. As the inert solvent to be employed, any one which is inert to the reaction can be used, as exemplified by water or alcohols such as methanol, ethanol, isopropanol, etc., ethers such as dioxane, tetrahydrofuran, etc., organic carboxylic acid such as acetic acid, propionic acid, etc., and further a mixture solvent thereof. The volume of the solvent is usually in the range of from about 3 to 50 weight parts relative to 1 weight part of the compound [I]. As the reducing catalyst, use is made of, for example, Raney nickel, stabilized nickel or metals of Group VIII such as palladium, platinum, rhodium, luthenium, cobalt, iron, etc. These metals are generally used in the metallic state, but may be used as salts, oxides or alloys. Among these reducing catalysts, palladium is especially useful. These catalysts can also be used as supported on a carrier e.g. activated charcoal, alumina, silica, diatomaceous earth, etc. The amount of these catalysts is in the range of 0.001 to 4 gram atom, preferably from 0.002 to 2 gram atom in terms of metal relative to 1 mole of the compound [I]. The reaction temperature ranges from 0° C. to 150° C., preferably from room temperatures to 80° C. The reaction proceeds even under normal pressure, but, more advantageously from the industrial point of view, at an elevated pressure, usually a pressure of 1 to 100 $kg/cm^2G$ as hdyrogen fractional pressure. The reaction completes in about 0.5 to 3 hours.

After completion of the reaction, the catalyst is removed by filtration, then the filtrate is subjected to conventional separation and purification means such as concentration, recrystallization, extraction, etc. to isolate the object compound in the free form or as a salt.

According to the method of this invention, the amount of the by-product, di(2-methyl-4-amino-5-pyrimidylmethyl)amine can be suppressed to 1% or less. The method of this invention has another advantage in that impurities such as 2-methyl-4-amino-5-hydroxymethylpyrimidine or Schiff base are not by-produced. Therefore, the yield of the object compound is high, and no complicated refining process is required, thus the method of this invention being very excellent from an industrial point of view. Also, the reaction mixture obtained when the compound [I] is prepared can be subjected to the catalytic reduction as it is, without isolating the compound [I]. Therefore, the method of preparing the compound [II] connected with the method of preparing the compound [I] is a very much advantageous industrial method.

Working examples are set forth as follows, by which the present invention is explained in more concrete manner. The NMR spectrum was obtained by determination with Varian T90 Type (90 MHz) or T100 Type (100 MHz) (δ value based on tetramethylsilane is expressed by ppm, and s means singlet and br means broad).

EXAMPLE 1

To a mixture of 27.4 g of 2-methyl-4-amino-5-formyl-pyrimidine and 1000 ml of methanol was added, while stirring at room temperature, dropwise gradually 25 ml of an aqueous solution containing 15.2 g of hydroxylamine hydrochloride. The reaction was allowed to proceed for further 3 hours at room temperature, which was then concentrated to dryness under reduced pressure. The concentrate was recrystallized from ethanol to give 25.6 g of 2-methyl-4-amino-5-pyrimidine aldoxime hydrochloride. The resulting mother liquor was concentrated to dryness under reduced pressure, followed by subjecting the concentrate to crystallization from a mixture of methanol/ether (1:1 V/V) to give 10.8 g of 2-methyl-4-amino-5-pyrimidine aldoxime hydrochloride. The total yield was 96.5%.

The physical properties of the first-obtained object compound are as follows:

Elemental Analysis for $C_6H_8N_4O \cdot HCl = 188.61$: Calcd.: C 38.21%, H 4.81%, N 29.70%. Found: C 38.03%, H 4.98%, N 29.40%.

NMR(90 MHz, DMSO-$d_6$): δ: 2.52(3H, s, $CH_3$), 8.24(1H, s, CH=N), 8.49, (1H, s, pyrimidine 6-H), 8.55(1H, br, NH), 9.57, (1H, br, NH), 11.88(1H, br, OH).

IR $\nu_{max}^{KBr}$ cm$^{-1}$: 3370, 1660, 1600, 1350, 990, 840, 780.

EXAMPLE 2

To 8.6 g of 2-methyl-4-amino-5-formylpyrimidine, while stirring at room temperature in a mixture of 200 ml of acetonitrile and 140 ml of water, was added dropwise gradually 10 ml of an aqueous solution containing 5.1 g of hydroxylamine hydrochloride. The reaction was allowed to proceed at room temperature for further 3 hours. A given volume of the reaction solution was taken as a sample, which was subjected to quantitative determination (by absolute calibration curve method) of 2-methyl-4-amino-5-pyrimidine aldoxime by means of high performance liquid chromatography [Column-Inert-Sil ODS (GASUKUROKOGYO, Inc., Japan) moving bed a mixture of ammonium phosphate, acetonitrile and triethylamine adjusted to pH 7 with phosphoric acid; detection UV(254 nm)] to thereby confirm that the yield was 9.37 g (98.3%).

EXAMPLE 3

To a mixture of 8.6 g of 2-methyl-4-amino-5-formyl-pyrimidine and 340 ml of methanol, while stirring at room temperature, was added dropwise gradually 40 ml of an aqueous solution of 5.20 g of hydroxylamine hydrochloride and 7.80 g of sodium carbonate. As the reaction proceeded, crystals precipitated. Four hours later, the crystals were collected by filtration, washed with methanol and water, followed by drying under reduced pressure to give 7.84 g (82.3%) of 2-methyl-4-amino-5-pyrimidine aldoxime. The mother liquor was subjected to high performance liquid chromatography to quantitatively determine 2-methyl-4-amino-5-pyrimidine aldoxime (by absolute calibration curve method) to confirm that 1.41 g (14.8%) of the object compound was produced. The total yield of the crystals and the object compound in the mother liquor was 97.1%. The mother liquor was concentrated to dryness under reduced pressure, followed by recrystallization from a mixture solvent of methanol/ether to isolate 0.8 g of 2-methyl-4-amino-5-pyrimidine aldoxime.

Physical properties of 2-methyl-4-amino-5-pyrimidine aldoxime first obtained were as follows:

Elemental Analysis for $C_6H_8N_4O = 152.156$: Calcd.: C 47.36%, H 5.30%, N 36.82%. Found: C 46.82%, H 5.32%, N 36.28%.

IR $\nu_{max}^{KBr}$ cm$^{-1}$: 3390, 3150, 1640, 1560, 1480, 970, 840

Physical properties of 2-methyl-4-amino-5-pyrimidine aldoxime isolated from the mother liquor were as follows:

Elemental Analysis for $C_6H_8N_4O = 152.156$: Calcd.: C 47.36%, H 5.30%, N 36.82%. Found: C 47.00%, H 5.30%, N 36.62%.

NMR(100 MHz, DMSO-$d_6$): δ: 2.36(3H, s, $CH_3$), 6.99(2H, br, $NH_2$), 7.45(1H, s, CH=N), 8.87(1H, s, pyrimidine-6H), 11.7 2(1H, br, OH).

IR $\nu_{max}^{KBr}$ cm$^{-1}$: 3420, 3140, 1670, 1590, 1550, 1490, 940, 770

EXAMPLE 4

To 8.6 g of 2-methyl-4-amino-5-formylpyrimidine, while stirring at room temperature in a mixture of 272 ml of methanol and 68 ml of water, was added dropwise 10 ml of an aqueous solution containing 5.1 g of hydroxylamine hydrochloride. The reaction was allowed to proceed for further 4 hours at room temperature. To the reaction solution was added dropwise 30 ml of an aqueous solution containing 3.90 g of sodium carbonate to cause precipitation of crystals. The crystals were collected by filtration and dried under reduced pressure to give 7.45 g (yield 78.2%) of 2-methyl-4-amino-5-pyrimidine aldoxime. The mother liquor was subjected to quantitative determination (by absolute calibration curve method) of 2-methyl-4-amino-5-pyrimidine aldoxime by means of high performance liquid chromatography to confirm that 1.95 g (yield 20.5%) of the object compound was produced. The total yield of the crystals thus obtained and the object compound in the mother liquor was 98.7%.

EXAMPLE 5

To 8.6 g of 2-methyl-4-amino-5-formylpyrimidine, while stirring at room temperature in a mixture of 340 ml of methanol and 40 ml of water, was added dropwise gradually 10 ml of an aqueous solution containing 6.10 g of hydroxylamine sulfate. As the reaction proceeded, crystals precipitated out. Four hours later, the crystals were collected by filtration, followed by drying under reduced pressure to give 10.5 g (83.5%) of 2-methyl-4-amino-5-pyrimidine aldoxime ½ sulfate. The mother liquor was subjected to quantitative deterimination (by absolute calibration curve method) of 2-methyl-4-amino-5-pyrimidine aldoxime ½ sulfate by means of high performance liquid chromatography to thereby confirm the production of 1.67 g (13.3%) of the object compound. The total yield of the crystals thus obtained and the object compound in the mother liquor was 96.8%. Physical properties of 2-methyl-4-amino-5-pyrimidine aldoxime ½ sulfate first obtained were as follows:
Elemental Analysis for $C_6H_8N_4O\cdot\frac{1}{2}H_2SO_4\cdot H_2O=219.211$: Calcd.: C 32.87%, H 5.06%, N 25.56%. Found: C 32.83%, H 4.82%, N 25.75%.

EXAMPLE 6

In 50 ml of methanol was suspended 6.8 g of 2-methyl-4-amino-5-formyl pyrimidine. To the suspension was added a solution of 3.8 g of hydroxylamine hydrochloride in 10 ml of water. To the mixture was further added 2.5 ml of 35% hydrochloric acid, which was warmed to 40° C. The solution was stirred for one hour, then a given volume of the reaction solution was taken, which was subjected to quantitative determination (by absolute calibration curve method) of 2-methyl-4-amino-5-pyrimidine aldoxime by means of high performance liquid chromatography to thereby confirm the production of 7.38 g (97.8%) of the object compound.

EXAMPLE 7

An autoclave of 300 ml capacity was charged with 3.75 g of 2-methyl-4-amino-5-pyrimidine aldoxime hydrochloride, 160 ml of methanol, 10 ml of acetic acid and 0.5 g of 5 wt% pd-C. The mixture was heated to 50° C. under stirring. Into the autoclave was introduced hydrogen gas with 40 kg/cm$^2$G, followed by allowing the reaction to proceed at 50° C. for one hour. The reaction mixture was cooled to room temperature, followed by separating the catalyst by filtration. The filtrate was subjected to high performance liquid chromatography (operation conditions including the column are the same as in Example 2) to conduct quantitative determination (by absolute calibration curve method) of each product. The yields of the respective products are as follows:
2-Methyl-4-amino-5-aminomethyl pyrimidine: 96%
Di-(2-methyl-4-amino-5-pyrimidylmethyl)amine: 0.5%
And, neither 2-methyl-4-amino-5-pyrimidylmethylidene-(2-methyl-4-amino-5-pyrimidylmethyl)amine nor 2-methyl-4-amino-5-hydroxylmethylpyrimidine was detected.

EXAMPLE 8

In 170 ml of methanol was dissolved 3.75 g of 2-methyl-4-amino-5-pyrimidine aldoxime hydrochloride. To the solution was added 0.7 g of 5 wt% pd-C, which was subjected to catalytic reduction in the same manner as in Example 7. The yields of the respective prodcuts were as follows:
2-Methyl-4-amino-5-aminomethylpyrimidine: 97%
Di-(2-methyl-4-amino-5-pyrimidylmethyl)amine: 0.5%
And, neither 2-methyl-4-amino-5-pyrimidylmethylidene-(2-methyl-4-amino-5-pyrimidylmethyl)amine nor 2-methyl-4-amino-5-hydroxymethylpyrimidine was detected.

EXAMPLE 9

In 170 ml of methanol was dissolved 3.75 g of 2-methyl-4-amino-5-pyrimidine aldoxime. To the solution was added 1.0 g of Raney.nickel, which was subjected to catalytic reduction in the same manner as in Example 7. The yields of the respective products were as follows:
2-Methyl-4-amino-5-aminomethylpyrimidine: 88%
Di-(2-methyl-4-amino-5-pyrimidylmethyl)amine: 0.7%
And, neither 2-methyl-4-amino-5-pyrimidylmethylidene-(2-methyl-4-amino-5-pyrimidylmethyl)amine nor 2-methyl-4-amino-5-hydroxymethylpyrimidine was detected.

EXAMPLE 10

To 170 ml of water was added 3.75 g of 2-methyl-4-amino-5-formylpyrimidine. To this mixture was added, while stirring at room temperature, dropwise 10 ml of an aqueous solution containing 2.6 g of hydroxylamine hydrochloride gradually. The reaction was allowed to proceed at room temperature for 4 hours. To the reaction mixture was added 1.3 g of 5 wt% pd-C, which was then put into an autoclave of 300 ml capacity. The temperature was raised up to 50° C. under stirring, then hydrogen gas was introduced into the autoclave to make the inner pressure 40 kg/cm$^2$G, followed by allowing the reaction to proceed at 50° C. for one hour. The reaction mixture was cooled to room temperature, then the catalyst was filtered off. By means of liquid chromatography, each product was quantitatively determined. The overall yield of each product based on 2-methyl-4-amino-5-formylpyrimidine was as follows:
2-Methyl-4-amino-5-aminomethylpyrimidine: 89%
Di-(2-methyl-4-amino-5-pyrimidylmethyl)amine: 0.1%
And, neither 2-methyl-4-amino-5-pyrimidylmethylidene-(2-methyl-4-amino-5-pyrimidylmethyl)amine nor 2-methyl-4-amino-5-hydroxylmethylpyrimidine was detected. And, 2-methyl-4-amino-5-pyrimidine aldoxime was contained in an amount of 6%.

EXAMPLE 11

To 170 ml of methanol was added 3.75 g of 2-methyl-4-amino-5-formyl pyrimidine. To the mixture was added dropwise gradually, while stirring at room temperature, 10 ml of an aqueous solution containing 2.6 g of hydroxylamine hydrochloride. The reaction was allowed to proceed at room temperature, followed by addition of 1.3 g of 5 wt% pd-C. Catalytic reduction was conducted, then the resultant was processed in the same manner as in Example 10. The overall yield of each procuct, based on the starting material 2-methyl-4-amino-5-formylpyrimidine was as follows:
2-Methyl-4-amino-5-aminomethylpyrimidine: 94%
Di-(2-methyl-4-amino-5-pyrimidylmethyl)amine: 0.6%
And, neither 2-methyl-4-amino-5-pyrimidylmethylidene-(2-methyl-4-amino-5-pyrimidylmethyl)amine nor 2-methyl-4-amino-5-hydroxylmethylpyrimidine was detected.

EXAMPLE 12

To 3.75 g of 2-methyl-4-amino-5-formylpyrimidine were added 135 ml of methanol and 35 ml of water. To the mixture was added dropwise gradually, while stirring at room temperature, 10 ml of an aqueous solution containing 2.60 g of hydroxylamine hydrochloride. The reaction was allowed to proceed at room temperature for 4 hours, followed by addition of 1.3 g of 5 wt% pd-C to conduct catalytic reduction. The reaction mixture was processed in the same manner as in Example 10. The overall yield of each product, based on the starting 2-methyl-4-amino-5-formylpyrimidine, was as follows:
2-Methyl-4-amino-5-aminomethylpyrimidine: 97%
Di-(2-methyl-4-amino-5-pyrimidylmethyl)amine: 0.4%
And, neither 2-methyl-4-amino-5-pyrimidylmethylidene-(2-methyl-4-amino-5-pyrimidylmethyl)amine nor 2-methyl-4-amino-5-hydroxylmethylpyrimidine was detected.

Subsequently, 50 ml of 1N hydrochloric acid was added to the reaction solution, and the mixture was concentrated under reduced pressure. To the concentrate was added 100 ml of methanol, then precipitating crystals were collected by filtration. The crystals were dried under reduced pressure to obtain 5.3 g (91%) of 2-methyl-4-amino-5-aminomethylpyrimidine.dihydrochloride. Content of di-(2-methyl-4-amino-5-pyrimidylmethyl)amine was 0.4%. The thus-obtained 2-methyl-4-amino-5-aminomethylpyrimidine.dihydrochloride has the following physical properties.

Elemental Analysis for $C_6H_{10}N_4.2HCl=211.094$: Calcd.: C 34.14%, H 5.73%, N 26.54%. Found: C 34.27%, H 5.78%, N 26.43%.

NMR(100 MHz, $D_2O$): δ: 2.64(3H, s, $CH_3$), 4.28(2H, s, $CH_2$), 8.35(1H, s, pyrimidine-6H).

IR $\nu_{max}^{KBr}$ cm$^{-1}$: 3000, 1680, 1640, 1610, 1530, 1380.

EXAMPLE 13

In 333 ml of methanol was dissolved 8.6 g of 2-methyl-4-amino-5-formylpyrimidine. To the solution was added gradually 10.6 g of phenyl hydrazine hydrochloride. As the reaction proceeded, crystals precipitated out. Five hours later, the crystals were collected by filtration and dried under reduced pressure to obtain 16.5 g (93%) of 1-(2-methyl-4-aminopyrimidyl)methylidene-2-phenylhydrazine hydrochloride. Physical properties of 1-(2-methyl-4-aminopyrimidyl)methylidene-2-phenylhydrazine hydrochloride are as follows:

Elemental Analysis for $C_{12}H_{13}N_5.HCl=263.730$: Calcd.: C 54.65%, H 5.35%, N 26.56%. Found: C 54.54%, H 5.37%, N 26.39%.

NMR(100 MHz, DMSO-$d_6$+$D_2O$) δ: 2.56(3H, s, $CH_3$), 7.05(5H, br, Ph), 8.01(1H, s, pyrimidine-6H), 8.39(1H, s, CH=N).

IR $\nu_{max}^{KBr}$ cm$^{-1}$: 3400, 2600, 1650, 1600, 1490, 1300, 1140, 750.

EXAMPLE 14

An autoclave of 300 ml capacity was charged with 3.75 g of 1-(2-methyl-4-aminopyrimidyl)methylidene-2-phenylhydrazine hydrochloride obtained in Example 13, 70 ml of methanol, 100 ml of acetic acid and 0.7 g of 5 wt% pd-C. The mixture was heated up to 50° C. under stirring, into which was introduced hydrogen gas with 40 kg/cm$^2$G. The mixture was stirred at 50° C. for 1 hour. A given volume of the reaction solution was taken, which was subjected to high performance liquid chromatography to determine quantitatively (by absolute calibration curve method) 2-methyl-4-amino-5-aminomethylpyrimidine to thereby confirm the production of 1.73 g (88%) of the object compound.

We claim:

1. A compound of the formula

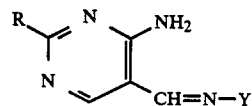

wherein

R is lower alkyl, and

Y is hydroxyl, amino, $C_{1-4}$ lower alkyl carbonylamino, $C_{1-3}$ lower alkyl amino or phenylamino, or a salt thereof.

2. A compound according to claim 1 wherein R is methyl.

3. A compound according to claim 1 wherein Y is hydroxyl.

4. A compound according to claim 2 wherein Y is hydroxyl.

5. A compound according to claim 1 wherein Y is phenylamino.

6. A compound according to claim 1 said compound being

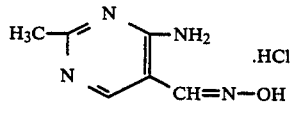

* * * * *